United States Patent [19]

Buechler

[11] Patent Number: 5,414,085
[45] Date of Patent: May 9, 1995

[54] BARBITURATE DERIVATIVES AND PROTEIN AND POLYPEPTIDE BARBITURATE DERIVATIVE CONJUGATES AND LABELS

[75] Inventor: Kenneth F. Buechler, San Diego, Calif.

[73] Assignee: Biosite Diagnostics, Inc., San Diego, Calif.

[21] Appl. No.: 864,110

[22] Filed: Apr. 6, 1992

[51] Int. Cl.⁶ .................. C07D 239/62; C07D 409/12
[52] U.S. Cl. ..................................... 544/300; 544/301
[58] Field of Search ................... 544/300, 301; 549/60

[56] References Cited

FOREIGN PATENT DOCUMENTS 0141393  5/1985  European Pat. Off. .

OTHER PUBLICATIONS

Förster, *Acta Biol. Med. Germ.*, vol. 9 (1962) pp. 497–516.
K. Foerster, et al., *Chemical Abstracts* 58:10665e, abstract of *Acta Biol. Med. Ger.*, 9, 497–516, 1962 (Ger) (1963).
Kotva, Rudolf et al., 5,5–Disubstituted Barbituric Acids and Their Analogues, Collection Czechoslovak Chem. Comm. 181:137–143 (1983).

*Primary Examiner*—Richard L. Raymond
*Attorney, Agent, or Firm*—Lyon & Lyon

[57] ABSTRACT

The present invention is directed to novel barbiturate derivatives which are synthesized for the covalent attachment to antigens (proteins or polypeptides) for the preparation of antibodies or receptors to the barbiturate metabolites. The resulting novel antigens may be used for the production of antibodies or receptors using standard methods. Once generated, the antibodies or receptors and the novel derivatives which are covalently attached to proteins, polypeptides or labels may be used in the immunoassay process.

2 Claims, 1 Drawing Sheet

EXAMPLE 2

EXAMPLE 3

EXAMPLE 4

BARBITURATE DERIVATIVES AND PROTEIN AND POLYPEPTIDE BARBITURATE DERIVATIVE CONJUGATES AND LABELS

FIELD OF THE INVENTION

This invention is in the field of ligand receptor assays, including immunoassays, for the detection of selected metabolites of barbiturates in a fluid sample. More particularly, this invention relates to methods for the synthesis of novel barbiturate derivatives and protein and polypeptide barbiturate derivative conjugates and labels for use in the preparation of antibodies to barbiturate metabolites and for use in the immunoassay process.

BACKGROUND OF THE INVENTION

The class of barbiturate derivatives is extensive and in general they are characterized by the amide urea ring with various alkyl substituents off the 5' position. Barbiturates are used as sedatives, hypnotics and to control seizures. The class of barbiturates includes, but is not limited to, amobarbital, aprobarbital, barbital, butabarbital, mephobarbital, pentobarbital, phenobarbital and secobarbital. The illicit and excessive use of barbiturates has resulted in a medical need for antibodies and diagnostics to rapidly detect the barbiturate metabolites in order to monitor and treat barbiturate addiction.

The preparation of antibodies to barbiturate metabolites requires the synthesis of a barbiturate derivative in order to covalently attach the derivative to an antigenic polypeptide or protein. In addition, the barbiturate derivative is covalently attached to various polypeptides, proteins or labels for use in screening antibodies and in the immunoassay process. The barbiturate derivative should mimic the structure of the class of barbiturate metabolites sought to be measured. Therefore, the selection and synthesis of the types of barbiturate derivatives for covalent attachment to proteins, polypeptides or labels is critical. In addition, the barbiturate derivatives need to be stable and soluble in an aqueous solution.

SUMMARY OF THE INVENTION

The present invention is directed to novel barbiturate derivatives which are synthesized for the covalent attachment to antigens (proteins or polypeptides) for the preparation of antibodies to the barbiturate metabolites. The resulting novel antigens may be used for the production of antibodies using standard methods. Once generated, the antibodies and the novel derivatives which are covalently attached to proteins, polypeptides or labels may be used in the immunoassay process.

DEFINITIONS

In accordance with the present invention and as used herein, the following terms, are defined with the following meanings, unless explicitly stated otherwise.

"Drug" shall mean any compound or ligand which either as a result of spontaneous chemical reaction or by enzyme catalyzed or metabolic reaction, generates an intrinsic activity when administered to a biological system. The drug may be metabolized to a derivative of the drug by a biological system. Common examples of drugs and their metabolites are morphine, barbiturates, tetrahydrocannabinol, phencyclidine, amphetamines, methamphetamines, opiates, benzodiazepines, cocaine, estrone-3-glucuronide, pregnanediol-glucuronide, cotinine, lysergic acid diethylamide, propoxyphene, methadone, anabolic steroids and tricyclic anti-depressants.

"Drug derivative" shall mean a ligand derivative, drug, drug metabolite or a drug analogue conjugated to a linking group.

"Drug metabolite" shall mean a compound upstream or downstream from a drug in a biochemical or metabolic pathway, or an intermediate.

"Label" shall mean a signal development element or a means capable of generating a signal, for example, a dye or an enzyme. The of a drug derivative attachment can be through covalent bonds, adsorption processes, hydrophobic and/or electrostatic bonds, as in chelates and the like, or combinations of these bonds and interactions.

"Binding domain" shall refer to the molecular structure associated with that portion of a receptor that binds ligand. More particularly, the binding domain may refer to a polypeptide, natural or synthetic, or nucleic acid encoding such a polypeptide, whose amino acid sequence represents a specific region of a protein, said domain, either alone or in combination with other domains, exhibiting binding characteristics which are the same or similar to those of a desired ligand/receptor binding pair. Neither the specific sequences nor the specific boundaries of such domains are critical, so long as binding activity is exhibited. Likewise, used in this context, binding characteristics necessarily includes a range of affinities, avidities and specificities, and combinations thereof, so long as binding activity is exhibited.

"Linking group" shall mean the composition between the protein, polypeptide or label and a drug or drug derivative. As one skilled in the art will recognize, to accomplish the requisite chemical structure, each of the reactants must contain the necessary reactive groups. Representative combinations of such groups are amino with carboxyl to form amide linkages, or carboxy with hydroxy to form ester linkages or amino with alkyl halides to form alkylamino linkages, or thiols with thiols to form disulfides, or thiols with maleimides or alkylhalides to form thioethers. Obviously, hydroxyl, carboxyl, amino and other functionalities, where not present may be introduced by known methods. Likewise, as those skilled in the art will recognize, a wide variety of linking groups may be employed. The structure of the linkage should be a stable covalent linkage formed to attach the drug or drug derivative to the protein, polypeptide or label. In some cases the linking group may be designed to be either hydrophilic or hydrophobic in order to enhance the desired binding characteristics of the ligand and the receptor. The covalent linkages should be stable relative to the solution conditions under which the ligand and linking group are subjected. Generally preferred linking groups will be from 1-20 carbons and 0-10 heteroatoms (NH, O, S) and may be branched or straight chain. Without limiting the foregoing, it should be obvious to one skilled in the art that only combinations of atoms which are chemically compatible comprise the linking group. For example, amide, ester, thioether, thioester, keto, hydroxyl, carboxyl, ether groups in combinations with carbon-carbon bonds are acceptable examples of chemically compatible linking groups. Other chemically compatible compounds which may comprise the linking group are set forth in this Definition section and hereby are incorporated by reference.

"Hydrocarbyl" shall refer to an organic radical comprised of carbon chains to which hydrogen and other elements are attached. The term includes alkyl, alkenyl, alkynyl and aryl groups, groups which have a mixture of saturated and unsaturated bonds, carbocyclic rings and includes combinations of such groups. It may refer to straight-chain, branched-chain cyclic structures or combinations thereof.

"Aryl" shall refer to aromatic groups which have at least one ring having a conjugated pi electron system and includes carbocyclic aryl, heterocyclic aryl and biaryl groups, all of which may be optionally substituted.

"Carbocyclic aryl groups" shall refer to groups wherein the ring atoms on the aromatic ring are carbon atoms. Carbocyclic aryl groups include monocyclic carbocyclic aryl groups and optionally substituted naphthyl groups.

"Monocyclic carbocyclic aryl" shall refer to optionally substituted phenyl, being preferably phenyl or phenyl substituted by one to three substituents, such being advantageously lower alkyl, hydroxy, lower alkoxy, lower alkanoyloxy, halogen, cyano, trihalomethyl, lower acylamino, lower amino or lower alkoxycarbonyl.

"Optionally substituted naphthyl" shall refer to 1- or 2-naphthyl or 1- or 2-naphthyl preferably substituted by lower alkyl, lower alkoxy or halogen.

"Heterocyclic aryl groups" shall refer to groups having from 1 to 3 heteroatoms as ring atoms in the aromatic ring and the remainder of the ring atoms carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl, and the like, all optionally substituted.

"Optionally substituted furanyl" shall refer to 2- or 3-furanyl or 2- or 3-furanyl preferably substituted by lower alkyl or halogen.

"Optionally substituted pyridyl" shall refer to 2-, 3- or 4-pyridyl or 2-, 3- or 4-pyridyl preferably substituted by lower alkyl or halogen.

"Optionally substituted thienyl" shall refer to 2- or 3-thienyl, or 2- or 3-thienyl preferably substituted by lower alkyl or halogen.

"Biaryl" shall refer to phenyl substituted by carbocyclic aryl or heterocyclic aryl as defined herein, ortho, meta or para to the point of attachment of the phenyl ring, advantageously para; biaryl is also represented as the —C$_6$H$_4$-Ar substituent where Ar is aryl.

"Aralkyl" shall refer to an alkyl group substituted with an aryl group. Suitable aralkyl groups include benzyl, picolyl, and the like, and may be optionally substituted.

"Lower" referred to herein in connection with organic radicals or compounds respectively defines such with up to and including 7, preferably up to and including 4 and advantageously one or two carbon atoms. Such groups may be straight chain or branched.

The terms (a) "alkyl amino", (b) "arylamino", and (c) "aralkylamino", respectively, shall refer to the groups —NRR' wherein respectively, (a) R is alkyl and R' is hydrogen or alkyl; (b) R is aryl and R' is hydrogen or aryl, and (c) R is aralkyl and R' is hydrogen or aralkyl.

The term "acyl" shall refer to hydrocarbyl—CO— or HCO—.

The terms "acylamino" refers to RCONCR)— and (RCO$_2$N-respectively, wherein each R is independently hydrogen or hydrocarbyl.

The term "hydrocarbyloxycarbonyloxy" shall refer to the group ROC(O)O— wherein R is hydrocarbyl.

The term "lower carboalkoxymethyl" or "lower hydrocarbyloxycarbonymethyl" refers to hydrocarbyl—OC(O)CH$_2$— with the hydrocarbyl group containing ten or less carbon atoms.

The term "carbonyl" refers to —C(O)—.

The term "carboxamide" or "carboxamido" refers to —CONR$_2$ wherein each R is independently hydrogen or hydrocarbyl.

The term "lower hydrocarbyl" refers to any hydrocarbyl group of ten or less carbon atoms.

The term "alkyl" refers to saturated aliphatic groups including straight-chain, branched chain and cyclic groups.

The term "alkenyl" refers to unsaturated hydrocarbyl groups which contain at least one carbon-carbon double bond and includes straight-chain, branched-chain and cyclic groups.

The term "alkynyl" refers to unsaturated hydrocarbyl groups which contain at least one carbon-carbon triple bond and includes straight-chain, branched-chain and cyclic groups.

The term "hydrocarbyloxycarbonylamino" refers to a urethane, hydrocarbyl—O—CONR— wherein R is H or hydrocarbyl and wherein each hydrocarbyl is independently selected.

The term "di(hydrocarbyloxycarbonyl)amino" refers to (hydrocarbyl—O—CO)$_2$N— wherein each hydrocarbyl is independently selected.

The term "hydrocarbylamino" refers to —NRR' wherein R is hydrocarbyl and R' is independently selected hydrocarbyl or hydrogen.

The term "mercapto" refers to SH or a tautomeric form.

The term "methene" refers to

The term "methylene" refers to —CH$_2$—.

The term "alkylene" refers to a divalent straight chain or branched chain saturated aliphatic radical.

The term "oxy" refers to —O— (oxygen).

The term "thio" refers to —S— (sulfur).

"Disulfide" refers to —S—S—.

"Thioester" refers to

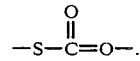

"Thioether" refers to C—S—C.

"Ester" refers to

"Analyte" shall mean substance of natural or synthetic origin sought to be detected and/or measured, said substance having a specific binding partner capable of a specific interaction with said analyte.

"Ligand" shall mean a binding partner to a ligand receptor. A substance which, if detected may be used to infer the presence of an analyte in a sample, including, without limitation, haptens, hormones, antigens, antibodies, deoxyribonucleic acid (DNA), ribonucleic acid (RNA), metabolites of the aforementioned materials and other substances of either natural or synthetic origin which may be of diagnostic interest and have a specific binding partner therefor, i.e., the ligand receptor of a ligand-receptor assay.

"Receptor" shall mean a receptor capable of binding ligand, typically an antibody, or a fragment thereof, but which may be another ligand, depending on assay design.

"Ligand-Receptor Assay" shall mean an assay for an analyte which may be detected by the formation of a complex between a ligand and a ligand receptor which is capable of a specific interaction with that ligand. Ligand-Receptor assays may be competitive or non-competitive, homogeneous or heterogeneous.

"Immunogen" shall mean a chemical or biochemical structure, determinant, antigen or portion thereof, which elicits an immune response, including, for example, polylysine, bovine serum albumin and keyhole limpid hemocyanin (KLH).

"Antigenic" shall mean a chemical or biochemical structure, determinant, antigen or portion thereof which is capable of inducing the formation of an antibody.

DETAILED DESCRIPTION OF THE PREFERRED EMBODIMENTS

Figure 1:
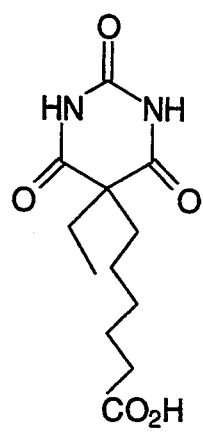
FIG. 1 depicts the structures of the compounds of Examples 2, 3, and 4.
Figure 1:
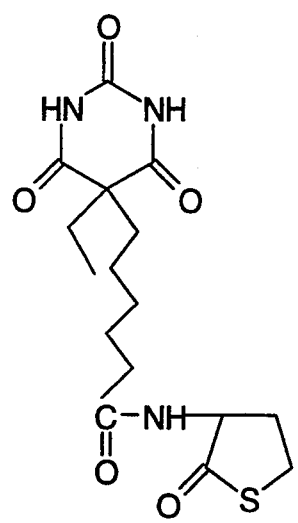
Figure 1:
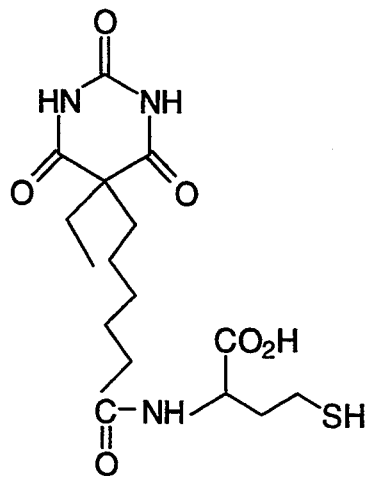

Novel compounds are described which are used in the generation of antibodies and in the immunoassay process generally. The compounds are derivatives of barbiturate metabolites. The derivatization of the barbiturate analogue for covalent attachment to proteins, polypeptides and labels occurs on the 5' carbon of the barbiturate ring. The synthesis of the linking group between the protein, polypeptide or label and the barbiturate derivative is designed to achieve the desired binding of the drug derivative and the receptor. For example, the derivative may be displaced from the surface of the protein, polypeptide or label to allow the derivative to present itself to the binding domain of receptors.

In general, the compounds of this invention have the following formula:

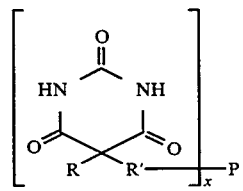

where R is hydrogen or a saturated or unsaturated aliphatic group or an aromatic group of from 1 to 10 carbons, either branched or straight chain;

where R' is a linking group comprising one of the following:

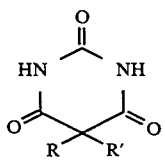

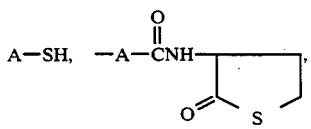

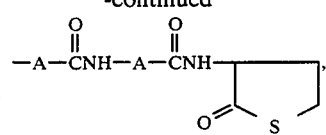

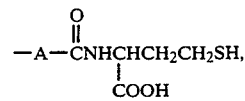

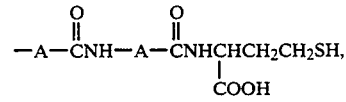

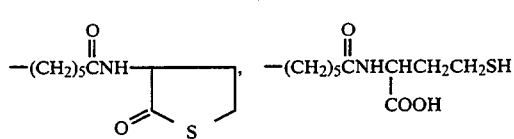

where A is a linking group of from 1 to 20 carbons and from 0 to 10 heteroatoms (NH, O, S), either branched or straight chain.

In addition, the general form of the immunogenic protein or polypeptide molecule or the protein or polypeptide molecule or label derivatized via an amide, disulfide, thioether, or ester bond to the molecule or label to a compound of the formula is of the following:

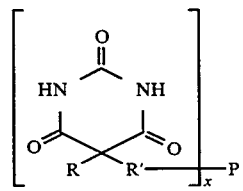

where P is an antigenic protein or polypeptide or a protein, polypeptide or label;

where x is at least one and not greater than 100;

where R is hydrogen or a saturated or unsaturated aliphatic group or an aromatic group of from 1 to 10 carbons, either branched or straight chain;

where R' is a linking group of the following:

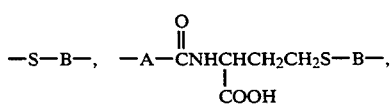

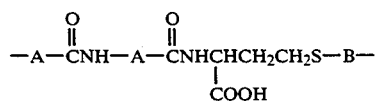

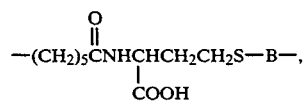

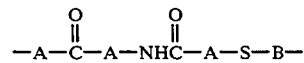

where A is a linking group of from 1 to 20 carbons and 0 to 10 heteroatoms (NH, O, S) either branched or straight chain;

where B is a linking group ultimately attached to a protein, polypeptide or label selected from the group comprising:

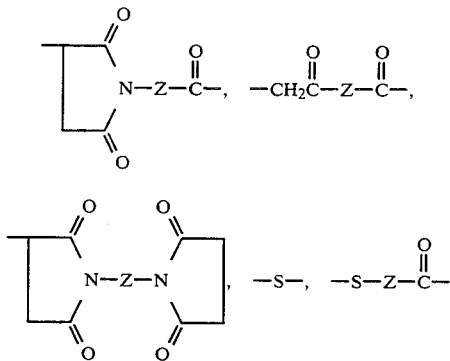

where Z is a linking group of from 1 to 20 carbons and 0 to 10 heteroatoms (NH, O, S) and may be branched or straight chain.

The preferred (best mode) compounds of this invention have the following formula:

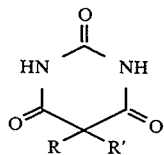

where R is —CH$_2$CH$_3$
where R' is a linking group comprising the following:

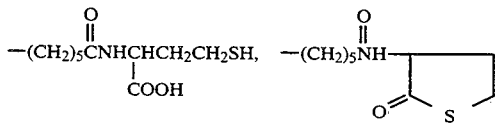

In addition, the preferred immunogenic (best mode) protein or polypeptide molecule or the protein or polypeptide molecule or label derivatized via an amide or ester bond to the molecule or label to a compound of the formula is of the following:

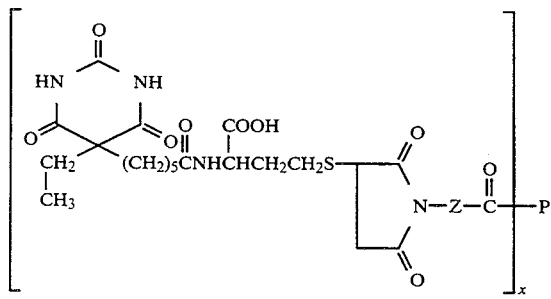

where P is an antigenic protein or polypeptide or a protein, polypeptide or label;
where x is at least one and not greater than 100;

where Z is a linking group of from 1 to 20 carbons and 0 to 10 heteroatoms (NH, O, S) and may be branched or straight chain.

The derivatization of the barbiturate derivative at the 5' carbon of the ring allows the partial elaboration of the linking group at step of synthesis of the malonic ester precursor. Various chain lengths of alkyl halide carboxylic acid esters, such as ethyl 6-bromohexanoate or ethyl 3-bromopropionate, can be reacted with, for example, diethylethyl malonate to form a barbiturate precursor with a linking group of various chain lengths. The barbiturate ring is then formed and the ester of the carboxylic ester is hydrolyzed. Various chain lengths of amino alkyl carboxylic acid esters can then be reacted with the carboxylic acid barbiturate acid to further extend the chain. The carboxylic acid barbiturate derivative so formed can be reacted with an amino alkyl thiol ester, for example, homocysteine thiolactone to form the thiol barbiturate derivative.

The barbiturate derivatives are synthesized as thiols or thiol esters so that their covalent attachment to proteins, polypeptides or labels can easily be performed under mild conditions, for example, pH 7 in a protein solution. The thiol esters of the resulting derivatives are hydrolyzed in dilute base, for example, 0.01M–0.1M potassium hydroxide, to generate the thiol group which is reacted with the thiol reactive group, such as a maleimide, an alkyl halide or a thiol. The thiol reactive group is generally on the protein, polypeptide or label but can also be incorporated onto the protein, polypeptide or label after the thiol drug reacts with the thiol reactive compound.

The protein, polypeptide or label is reacted with a reagent which incorporates a maleimide or alkylhalide into the molecule. These reagents and methods for their use are available from Pierce, Rockford, Ill., for example, for incorporation of maleimide groups onto proteins, polypeptides or labels one can use succinimidyl 4-(N-maleimidomethyl)cyclohexane-1-carboxylate (SMCC), succinimidyl 4-(p-maleimidophenyl)butyrate (SMPB) or m-maleimidobenzoyl-N-hydroxysuccinimide ester (MBS). For introduction of an alkyl halide into a protein, polypeptide or label one can use N-succinimidyl(4-iodoacetyl)aminobenzoate (SIAB) also from Pierce. The thiol reactive group, such as maleimide, an alkyl halide or a thiol can be incorporated into the protein, polypeptide or label prior to reaction with the drug thiol, but the drug thiol can also be reacted with the thiol reactive compound prior to reaction with the protein, polypeptide or label. Also, bis-maleimide compounds of varying length can be reacted with thiol containing proteins, polypeptides or labels for covalent coupling of the barbiturate thiol derivatives. Conversely, the bis-maleimide compound can be reacted with the thiol derivative and subsequently to the thiol containing protein, polypeptide or label. Common bis-maleimides are bis-maleimidohexane from Pierce, N,N'-bis(3-maleimidopropionyl)-2-hydroxy-1,3-propanediamine from Sigma Chemical Co., St. Louis, Mo., and 1,1'-(methylenedi-4,1-phenylene)-bismaleimide from Aldrich Chem. Co., Milwaukee, Wis. The thiol barbiturate derivatives can also form disulfides with a thiol containing polypeptide, protein or label molecules as a means to incorporate the derivative into the molecule.

The use of drug derivatives, immunogens and protein and polypeptide conjugates for generating antibodies and for use in the immunoassay process is described, for example, in U.S. Pat. Nos. 5,028,535 and 5,089,391.

EXPERIMENTAL EXAMPLES

EXAMPLE 1

Synthesis of Ethyl-5-Carboxypentyldiethylmalonate

Sodium metal (1.84 g, $8.0 \times 10^{-2}$ mol) was dissolved in ethyl alcohol (60 ml) and to the resulting solution was added diethyl ethylmalonate (7.5 g, $4.0 \times 10^{-2}$ mol) followed by 6-bromohexanoic acid (7.8 g, $4.0 \times 10^{-2}$ mol). The mixture was refluxed under argon with stirring for 1 hour and allowed to cool. The solvent was evaporated and the residue was dissolved in water (100 ml) and extracted with diethyl ether ($2 \times 60$ ml). The aqueous layer was acidified with 6N hydrochloric acid (16 ml) and extracted with diethyl ether ($1 \times 100$ ml). The organic layer was washed with water (40 ml), dried over anhydrous magnesium sulfate and filtered. The filtrate was evaporated under vacuum to afford 7.0 g (58%) of ethyl 5-carboxypentyldiethylmalonate as a clear oil.

EXAMPLE 2

Synthesis of 5-Ethyl-5'-(5-Carboxypentyl) Barbituric Acid

Sodium metal (2.1 g, $9.1 \times 10^{-2}$ mol) was dissolved in ethyl alcohol (100 ml) and to the resulting solution was added urea (4.2 g, $7.0 \times 10^{-2}$ mol). The mixture was stirred at room temperature until all the urea had dissolved (ca. 30 minutes) and a solution of ethyl 5-carboxypentyldiethylmalonate (7.0 g, $2.3 \times 10^{-2}$ mol) in ethyl alcohol (20 ml) was added. The mixture was refluxed under argon with stirring for 20 hours and allowed to cool. The solvent was evaporated and the residue was dissolved in 1N hydrochloric acid (120 ml) and extracted with diethyl ether ($1 \times 120$ ml). The organic layer was washed with water ($1 \times 50$ ml), dried over anhydrous magnesium sulfate and filtered. The filtrate was evaporated under vacuum and the residual solid was treated with hexane/diethyl ether (3:2) and was collected by filtration to afford 1.8 g (29%) of 5-ethyl-5-(5-carboxypentyl) barbituric acid as a white solid: mp 185°–192° C.

EXAMPLE 3

Synthesis of 5-Ethyl-5'-[6-(2-Amino-4-Thiolbutanoic Acid Thiolactone)-Hexanamide] Barbituric Acid To a stirring solution of 5-ethyl-5-(5-carboxypentyl) barbituric acid (1.8 g, $6.7 \times 10^{-3}$ mol) in anhydrous dimethyl formamide (60 ml) was added anhydrous pyridine (1.2 ml, $1.5 \times 10^{-2}$ mol) followed by 1-(3-dimethylaminopropyl)-3-ethylcarbodiimide hydrochloride (1.4 g, $7.3 \times 10^{-3}$ mol). The mixture was stirred under argon at room temperature for 4 hours. The solvent was evaporated and the residue was dissolved in water (80 ml) and extracted with ethyl acetate (80 ml). The organic layer was washed with water ($2 \times 80$ ml), dried over anhydrous magnesium sulfate and filtered. The filtrate was evaporated under vacuum to afford 1.8 g (73%) of the title compound as a clear colorless foam.

EXAMPLE 4

Synthesis of 5-Ethyl-5'-[6-Cysteine)-Hexanamide] Barbituric Acid

5-Ethyl-5'-[6-(2-amino-4-thiolbutanoic acid thiolactone)-hexanamide] barbituric acid (0.01 g, $2.7 \times 10^{-5}$ mol) was dissolved in 1.08 ml dimethylformamide/water (70/30, v/v). Potassium hydroxide (0.271 ml, 1N) was added and the solution sat at room temperature for 5 min. Potassium phosphate buffer (0.3 ml, 0.5M, pH 7), was immediately added and the solution was adjusted to pH 7–7.5 with hydrochloric acid (1N). The title compound in solution was used as is to react with thiol reactive groups, such as maleimides, alkyl halides or thiols, which are either free in solution or are coupled to proteins, polypeptides or labels.

Other embodiments are within the following claims.

I claim:

1. Compounds of the formula:

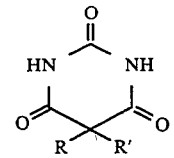

where R is hydrogen, a saturated or unsaturated aliphatic group of from 1 to 10 carbons, either branched or straight chain, or an aryl group;

where R' is a linking group comprising one of the following:

A—SH,

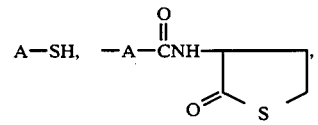

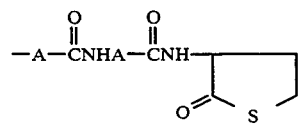

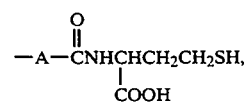

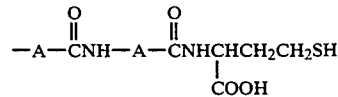

where A is a linking hydrocarbyl group of from 1 to 20 carbon atoms and 0 to 10 heteroatoms selected from the group consisting of nitrogen, oxygen, and sulfur, which may be positioned either in a chain or substituted on the chain, except in A—SH where A is not methylene, ethylene, propylene, butylene, or pentylene when R is —$CH_2$—$CH_2SH$, 2-butenyl or isopentyl.

2. Compounds of the formula:

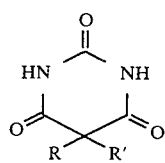
where R is —CH$_2$CH$_3$
where R is a linking group consisting of the following;
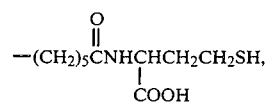
and
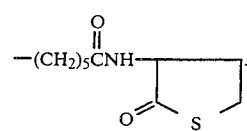
* * * * *